United States Patent
Burkhardt et al.

(10) Patent No.: US 6,444,862 B1
(45) Date of Patent: Sep. 3, 2002

(54) SYNTHESIS AND ISOLATION OF METAL ALKOXIDES

(75) Inventors: Elizabeth R. Burkhardt, Bridgeville; Joseph A. Corella, II, Zelienople; David H. Ellenberger, Karns City; Christopher P. Sutton, Mars, all of PA (US)

(73) Assignee: Mine Safety Appliances Company, Pittsburgh, PA (US)

( * ) Notice: Subject to any disclaimer, the term of this patent is extended or adjusted under 35 U.S.C. 154(b) by 0 days.

(21) Appl. No.: 09/580,107

(22) Filed: May 30, 2000

(51) Int. Cl.$^7$ ............................................. C07C 31/30
(52) U.S. Cl. ................................................. 568/851
(58) Field of Search ................................. 568/851, 875

(56) References Cited

U.S. PATENT DOCUMENTS 4,748,283 A * 5/1988 Kamienski .................. 568/851
5,276,219 A * 1/1994 Schwindeman et al. .... 568/851

FOREIGN PATENT DOCUMENTS

EP          0 192 608        8/1986
WO         WO 00/58380      10/2000

OTHER PUBLICATIONS

Rautenstrauch, Valentin: "Potassium Carboxylates by Direct Carbonylation of Potassium Alkoxides", *Helvetica Chimica Acta*, vol. 70 (May 1987) pp. 593–599, English, XP002185913.

Cuvigny, Therese: "Alkylation du linalol sur les carbones $C_8$ (et $C_6$)", *Journal of Organometallic Chemistry*, 344 (1988) pp. 9–28, French, XP002185914.

Kabaki et al.: "Reaction of Triorgano(triorganogermyl)silanes with Alkali–Metal Allyl Alcoholates", *Synthetic Communications*, 22(3), (1992), pp. 459–466, English, XP001042160.

Smith et al.: "Sytrene–Diene Random Copolymers, Blends and 'Random–Diblock' Coplymers", (Aug. 1994), pp. 466–467, English, XP001042132.

Ndebeka et al.: "Alkoxide Variation in Complex Base–Promoted Syn Dehydrohalogenations", *J. Org. Chem.* (Dec. 19,1980), pp. 5394–5396, English, XP002185915.

Quast et al.: "Ein Diazaphosphiridin–3–oxid$^{1b)}$", *Liebigs Ann. Chem.*, (May 1987), pp. 967–976, German, XP002185916.

Bauer et al: "Structure of a Super Base in Tetrahydrofuran Solution Studied by $^6$Li, $^1$H Hoesy, $^{133}$Cs, $^1$H Hoesy, and MNDO. Evidence for Discrete Species Rather Than a Mixed Aggregate", *J. Am. Chem. Soc.* (Sep. 1992), 114, pp. 7482–7489, English, XP002185917.

Beck et al.: "Lipophilic Lithium Alkoxides or Dialkylboroxides; X–Ray Structures of [Li($\mu$–OR')]$_2$ and Li(OBR$_2$)(tmeda), [tmeda=(Me$_2$NCH$_2$)$_2$, R=CH(SiMe$_3$)$_2$, R'=Cbu$^{t3}$ or BR$_2$]†", *J. Chem. Soc., Chem. Commun.* (Sep 1989), pp. 1312–1314, English, XP002185918.

Tseng et al.: "Skipped Diynes—VI: Triethylnylcarbinols, Related Diynes and Allene Dimers", *Tetrahedron*, vol. 30, pp. 377–383 English, Pergamon Press 1974, XP002185919.

Russell et al.: "Carboxylative Coupling of Propargylic Alcohols with Allyl Chloride", *J. Org. Chem.* (Dec 1986), pp. 5499–5501, English, XP002185920.

Kahn et al.: "Mass Spectrometry of Gas–Phase Lithium Alkoxides", *J. Phys. Chem.* (Jan 1988), pp. 212–220, English, XP001042133.

* cited by examiner

*Primary Examiner*—Samuel Barts
*Assistant Examiner*—Elvis O. Price
(74) *Attorney, Agent, or Firm*—J. G. Uber; H. E. Bartony, Jr.

(57) ABSTRACT

A method for synthesizing highly soluble metal alkoxides includes the step of reacting a tertiary alcohol having the formula:

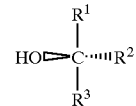

wherein $R^1$, $R^2$, and $R^3$ are, independently, the same or different, an alkyl group, an alkenyl, an alkynyl group or an aryl group, and at least one of $R^1$, $R^2$, and $R^3$ is a group of at least 3 carbon atoms, with at least a stoichiometric amount of a metal reagent. The metal reagent is generally a group I metal, a group II metal, zinc, a metal alloy of a group I metal, a metal alloy of a group II metal, a metal alloy of zinc, a compound of a group I metal, a compound of a group II metal or a compound of zinc.

5 Claims, 2 Drawing Sheets

SYNTHESIS AND ISOLATION OF METAL ALKOXIDES

FIELD OF THE INVENTION

The present invention relates to metal alkoxides and to the preparation and isolation of metal alkoxides, and especially, to metal alkoxides that are liquid when pure and/or exhibit increased solubility in a wide variety of solvents, and to methods of preparation of such metal alkoxides.

BACKGROUND OF THE INVENTION

Metal alkoxides, and particularly alkali metal alkoxides, are widely used in industry as catalysts and as stoichiometric reagents. These reagents are used in diverse reaction chemistries such as alkylation, isomerization, rearrangements, condensations, transesterifications and eliminations. See, for example, D. E. Pearson, C. A. Buehler Chemistry Reviews 74, 45 (1974).

As pure solid compounds, these materials are ionic in character as a result of the strongly electropositive nature of the metals. See, for example, D. C. Bradley, R. C. Mehrotra, D. P. Gaur, *Metal Alkoxides*, Academic Press, London (1978). For derivatives of the same element, the covalent character of the metal-oxygen bond increases with the greater inductive effect of the alkyl group. For example, a tertiary butoxide has a higher covalent character than the corresponding primary n-butoxide. The trend in covalent character relative to the counter ion in the case of alkali metals, for example, is that lithium alkoxides are more covalent than sodium or potassium alkoxides. This phenomenon, coupled with steric factors, leads to a slightly greater inherent stability of the isolated solid tertiary alkoxides. Unfortunately, these caustic solids readily react with atmospheric water and carbon dioxide. Furthermore, these solid metal alkoxides are rather dusty, which can be problematic when handled on a large scale. Some of the primary alkoxides are also prone to spontaneous combustion in air. See Y. El-Kattan, J. McAtee, "Sodium Methoxide" *Encyclopedia of Reagents for Organic Synthesis*, 4593, Ed. L. A. Paquette, John Wiley and Sons, NY (1995).

To provide a safer material, metal alkoxides are often dissolved in a solvent. In general, liquids are, for example, easier to transfer from drums or cylinders into reactors (reducing the exposure of human handlers to dangerous materials), more easily kept under an inert atmosphere, and provide more options for modes of addition to the substrate. Unfortunately, alkali metal alkoxides and other metal alkoxides exhibit only rather low solubility in the alcohols from which the alkoxides are made, usually in the range of 2–25 wt %. For example, sodium isopropoxide is only soluble up to about 2 wt % in isopropanol. The low solubilities of many alkoxides have been attributed to the ionic character and the extent of oligomerization or polymerization in solution. Another factor affecting solubility in an alcohol solvent is the propensity of alkoxides to form insoluble alcoholate complexes with the alcohol. Metal alkoxides are somewhat more soluble in polar ethereal solvents such as tetrahydrofuran and the polyethers (glymes). However, even in ethers, the solubility is generally less than 50%, especially at or below room temperature (that is, at or below 25° C.). Moreover, the range of polar solvents is somewhat limited as a result of the reactivity of the alkoxide. Furthermore, in some cases the solvent of choice for the desired reaction involving a metal alkoxide is not compatible with the alkoxide or the metal alkoxide is insoluble therein.

It is very desirable to develop metal alkoxide reagents that facilitate the diverse reactions in which those reagents are use.

SUMMARY OF THE INVENTION

The present invention provides generally a method to produce relatively highly concentrated solutions of metal alkoxides in a wide variety of solvents. Solvents suitable for use in the present invention include aliphatic and aromatic hydrocarbons, and polar aprotic solvents such as dimethylformamide (DMF) and ethers. Preferably, the solubility of the metal alkoxide in the solvent is at least approximately 25 wt %. More preferably, the solubility of the metal alkoxide in the solvent is at least approximately 50 wt %. Most preferably, the solubility of the metal alkoxide in the solvent is at least approximately 75 wt %. These solubilities are achievable at relatively low temperature. Preferably, for example, these solubilities are exhibited in a temperature range of approximately −40° C. to approximately 50° C. More preferably, these solubilities are exhibited in a temperature range of approximately −25° C. to approximately 25° C. Most preferably, these solubilities are exhibited in a temperature range of approximately 0° C. to approximately 25° C. Surprisingly, the relatively high solubilities of the present invention are achievable even in aliphatic hydrocarbons and aromatic hydrocarbons.

The present invention also provides for isolation and characterization of the first pure liquid alkali metal alkoxide reagent and other liquid metal alkoxide reagents. As used herein, the terms "pure" or "neat" refer to a liquid having a purity of at least approximately 97 wt % (that is, the liquid is at least 97% metal alkoxide by weight). The purity is more preferably at least approximately 98 wt %. Most preferably, the purity is at least approximately 99 wt %. Unlike current metal alkoxide reagent compositions, the neat, liquid alkoxide reagents of the present invention are highly miscibile in all proportions with a wide variety of solvents, including, for example, aliphatic hydrocarbon solvents such as hexane and heptane or aromatic hydrocarbon solvents. Other suitable solvents include ethers and polar aprotic solvents. Furthermore, the compositions of the present invention are relatively easy to handle or transport. Moreover, the highly concentrated and/or neat liquid metal alkoxide reagents of the present invention allow higher reactor loading than is possible with current compositions, thereby maximizing productivity.

In one aspect, the present invention provides a method for synthesizing highly soluble metal alkoxides comprising the step of: reacting a tertiary alcohol with at least a stoichiometric amount of a metal reagent. Preferably, the reaction proceeds for a period of time sufficient for the reaction to go to completion. The metal reagent is preferably a group I metal, a group II metal, zinc, a metal alloy of a group I metal, a metal alloy of a group II metal, a metal alloy of zinc (suitable metal alloys, include, for example, NaK, NaHg or KHg), a compound of a group I metal, a compound of a group II metal or a compound of zinc (suitable, metal compounds include, for example, LiH, NaH, KH, $Et_2Zn$ or $Bu_2Mg$) Preferred metals for use in the present invention include K, Li, Na, Cs, Mg, Ca or Zn. Likewise, metal alloys and metal compounds for use in the present invention preferably include K, Li, Na, Cs, Mg, Ca or Zn. In the case that a metal is used, the reaction preferably takes place above the melting point of the metal. Preferably, formation of a metalalcoholate complex is avoided. To avoid forming a metalalcoholate complex, an excess of metal reagent (for example, metal, metal alloy and/or metal compound) is preferably used.

Tertiary alcohols suitable for use in the present invention preferably have the general formula:

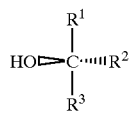

(or HOCR$^1$R$^2$R$^3$) wherein R$^1$, R$^2$, and R$^3$ are, independently, the same of different, an alkyl group, an alkenyl group, an alkynyl group or an aryl group, and at least one of R$^1$, R$^2$, and R$^3$ is a group of at least 3 carbon atoms. Preferably, at least on of R$^1$, R$^2$, and R$^3$ is a branched group of at least 3 carbon atoms. More preferably, at least one of R$^1$, R$^2$, and R$^3$ is a branched group of at least 6 carbon atoms. As used herein, the term "alkyl group" includes generally branched and unbranched alkyl group of the formula —C$_n$H$_{2n+1}$ (wherein n is an integer) and cyclic alkyl groups of the formula —C$_m$H$_{2m}$ wherein m is an integer equal to or greater than 3. Alkyl groups preferably have 1 to 20 carbons. The term "alkenyl" refers generally to a straight or branched chain hydrocarbon group with at least one double bond, preferably with 2–20 carbon atoms, and more preferably with 3–10 carbon atoms (for example, —CH=CHR, —CH$_2$CH=CHR, or —CH$_2$CH=CHCH$_2$CH=CHR, wherein R is, for example, H, an alkyl group, an alkenyl group, an alkynyl group or an aryl group). The term "alkynyl" refers to a straight or branched chain hydrocarbon group with at least one triple bond, preferably with 2–20 carbon atoms, and more preferably with 3–10 carbon atoms (for example, —C≡CR, —CH$_2$C≡CR, or —CH$_2$C≡CCH$_2$C≡CR). The term "aryl group" preferably includes generally phenyl and napthyl groups. The term "branched" as use herein refers generally to a group that has at least one carbon atom attached to at least three other carbon atoms. Examples of branched groups include, but are not limited to, cyclic alkyl groups, aryl groups, arylalkyl groups and branched acyclic alkyl groups (for example, an isopropyl group). The alkyl, alkenyl, alkynyl and/or aryl groups of the present invention can be substituted or unsubstituted. Alkyl groups can, for example, be substituted with (that is, one or more of the hydrogen atoms thereof replaced with) an aryl group (making an arylalkyl group), an alkenyl group and/or an alkynyl group. Alkenyl groups can, for example, be substituted with an alkyl group and/or an aryl group. Alkynyl groups can, for example, be substituted with an alkyl group and/or an aryl group. Aryl groups can, for example be substituted with an alkyl group, an alkenyl group and/or an alkynyl group.

In another aspect, the present invention provides a solution of a metal alkoxide of the formula:

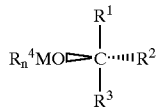

(or R$^4_n$MOCR$^1$R$^2$R$^3$), wherein R$^4$ is an alkyl group, an aryl group or an alkoxyl group, M is a group I metal, a group II metal or zinc, and n is 0 or 1. M is preferably K, Li, Na, Cs, Mg, Zn or Ca. The concentration of metal alkoxide in the solvent is preferably greater than 50 wt %. More preferably, the concentration of the metal alkoxide is at least 75%. If M is a monovalent metal ion, n is 0. If M is a divalent metal ion, n is 1. Suitable solvents include aliphatic hydrocarbons, aromatic hydrocarbons, and polar aprotic solvents. As used herein, the term "alkoxyl group" refers generally to groups having the formula —OR$^5$, wherein R$^5$ is an alkyl group (substituted or unsubstituted). R$^5$ can, for example, be —CR$^1$R$^2$R$^3$.

In still another aspect, the present invention provides a compound having the formula:

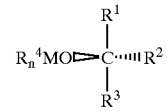

(or R$^4_n$MOCR$^1$R$^2$R$^3$), wherein M, R$^1$, R$^2$, R$^3$, R$^4$ and n are as defined above. Unlike prior metal alkoxide reagents, the metal alkoxides of the present invention are liquid at or below 25° C. and having a purity greater than approximately 97 wt %. Examples of such metal alkoxide compounds include, but are not limited to, potassium, sodium and lithium (3,7-dimethyl-3-octanoxide), .

DETAILED DESCRIPTION OF THE INVENTION

Figure 1:
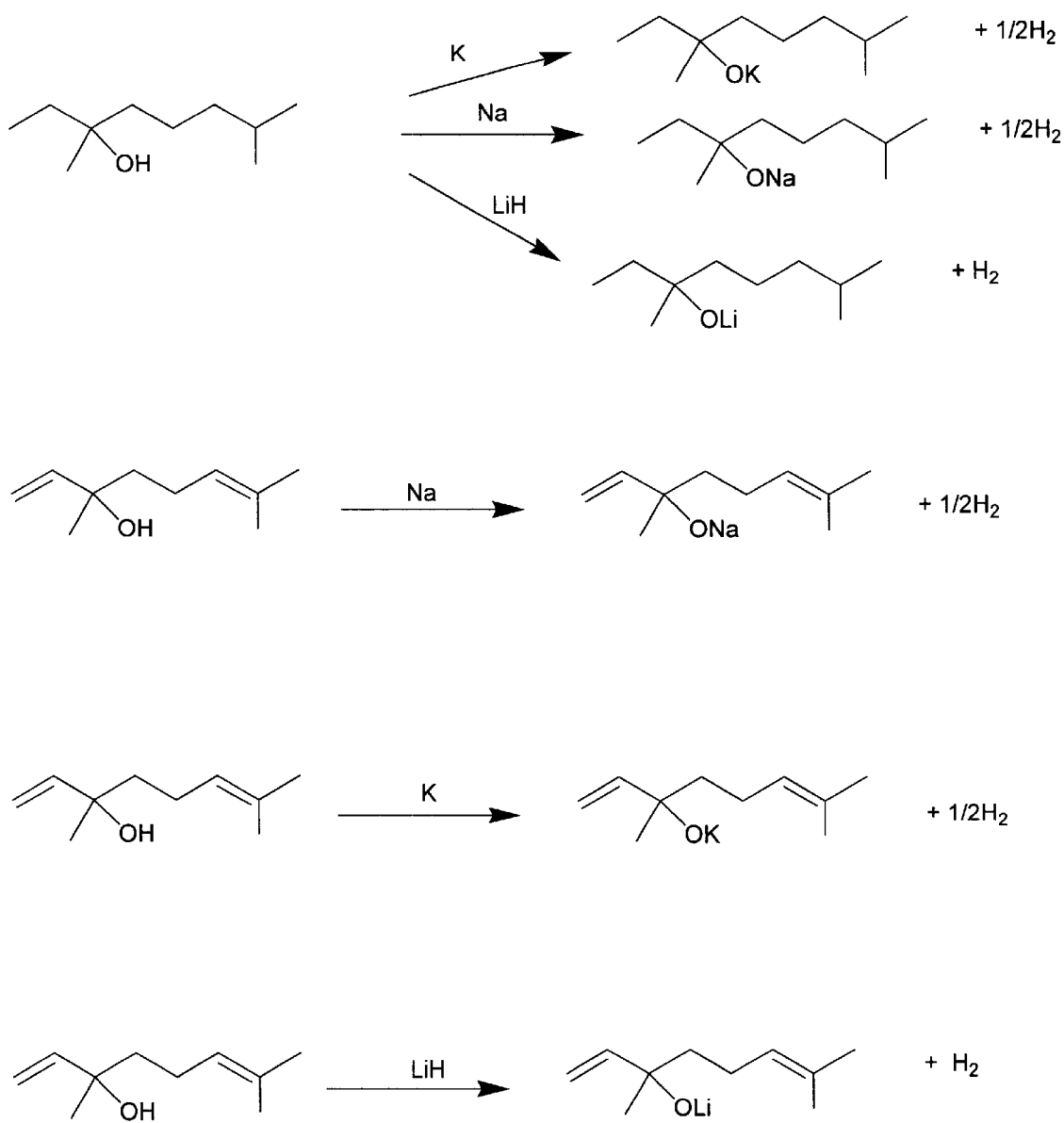
FIG. 1 illustrates chemical reactions of alkali metals and alkali metal compounds with 3,7-dimethyl-3-octanol or with linalool to produce the corresponding alkali metal alkoxides.
Figure 2:
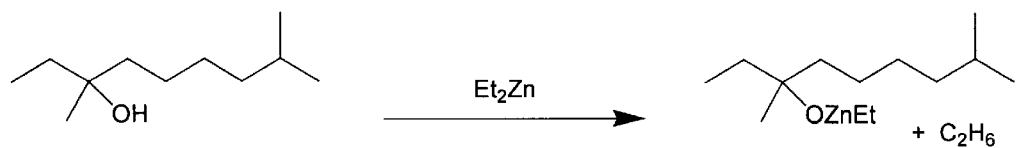
FIG. 2 illustrates a chemical reaction of diethylzinc with 3,7-dimethyl-3-octanol to produce the corresponding ethyl zinc 3,7-dimethyl-3-octanoxide.
Figure 3:
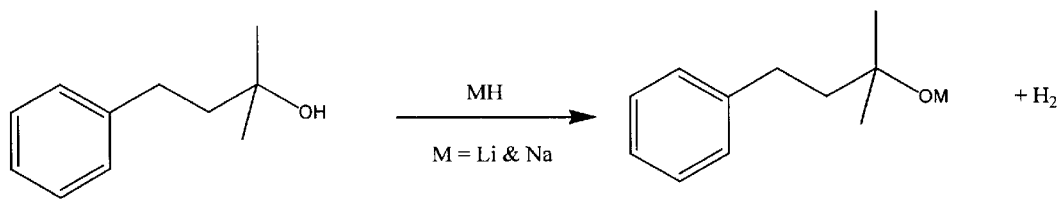
FIG. 3 illustrates the chemical reaction of two other tertiary alcohols with a metal to form the corresponding liquid metal alkoxide.
Figure 3:
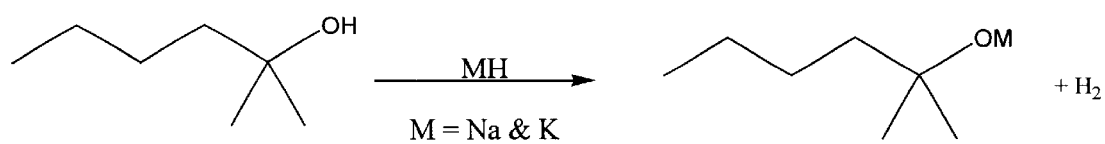

In general, the present invention provides metal alkoxides of increased solubility in a broad range of solvents. Moreover, for the first time, a number of the metal alkoxides of the present invention were isolated as a neat liquid (that is, substantially pure or substantially solvent free as defined above). In general, the metal alkoxides of the present invention are preferably synthesized from tertiary alcohols with at least one branched substituent.

For example, a new alkoxide has been prepared by reacting potassium metal with 3,7-dimethyl-3-octanol in a hydrocarbon solvent. The resulting alkoxide, potassium 3,7-dimethyl-3-octanoxide (KDMO), can be produced as high weight percent solutions and is a liquid when neat. In addition, the sodium and lithium alkoxides of 3,7-dimethyl-3-octanol were found to be liquids when pure. Other liquid metal alkoxides can be made from this alcohol with a counterion of, for example, calcium, magnesium, or zinc.

Other tertiary alcohols can be easily converted into alkoxides by the same methods as described for the alkali metal 3,7-dimethyl-3-octanoxide. Tertiary alcohols suitable for use in the present invention preferably have the general formula:

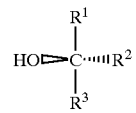

(or HOCR$^1$R$^2$R$^3$) wherein R$^1$, R$^2$, and R$^3$ are, independently, the same of different, an alkyl group, an alkenyl group, an alkynyl or an aryl group, and at least one of R$^1$, R$^2$, and R$^3$ is a group of at least 3 carbon atoms as described above. Examples of alcohols suitable for use in the present invention include, but are not limited to, 3,7-dimethyl-3-octanol, linalool, dimethylbenzenepropanol, 2-methyl-2-hexanol and 3-ethyl-2,2-dimethyl-3-pentanol.

The metal alkoxides of the present invention are preferably prepared by the reaction of a metal and the corresponding alcohol. Other synthetic methods involving the reaction of metal alloys (for example, NaK) or metal compounds (for example, metal hydrides, metal hydroxides or alkylmetal compounds) are also suitable. However, synthetic methods using metal alloys or metal compounds (rather than the corresponding metal) can be either quite expensive or result in metal alkoxide products of lower purity. Reaction of the metal and the corresponding alcohol is thus preferred when possible in the present invention.

In the case of alkali metal alkoxides, potassium tertiary alkoxides are stronger bases than primary and secondary alkoxides of potassium, sodium or lithium when compared in the same solvent. Another property of tertiary alkoxides is their relatively weak nucleophilicity. As a result, interfering reaction pathways to impurities are diminished. A tertiary potassium alkoxide produced from an alcohol such as 3,7-dimethyl-3-octanol displays such desirable properties. In the case of 3,7-dimethyl-3-octanol, $R^1$ is a methyl group, $R^2$ is an ethyl group and $R^3$ is a 4-methyl pentyl group.

In one set of studies, potassium 3,7-dimethyl-3-octanoxide (KDMO), was prepared by the reaction of potassium metal with 3,7-dimethyl-3-octanol in heptane in a pressure reaction vessel. The alcohol was metered into a molten potassium dispersion in the solvent. Reaction temperatures were preferably maintained above 100° C. For example, in several experiments the reaction temperature was maintained at approximately 110° C., followed by a heat soak at 125–130° C. for at least approximately 2 hours. The reaction pressures were generally above 1 atm. In several studies, the potassium alkoxide solution was prepared as a 50 wt % solution in heptane. Further studies demonstrated that 70–75 wt % solutions were easily prepared by the same method. Hydrocarbon solvents other than heptane, as well as ether solvents (for example, tetrahydrofuran) or polar aprotic solvents can also be used in the synthetic methods of the present invention. Furthermore, the neat potassium 3,7-dimethyl-3-octanoxide can be prepared without solvent by addition of potassium to neat 3,7-dimethyl-3-octanol (one equivalent).

Potassium 3,7-dimethyl-3-octanoxide was subsequently isolated by vacuum distillation of the heptane from the product. The pure potassium alkoxide exists as a liquid. Attempts to induce crystallization of the potassium 3,7-dimethyl-3-octanoxide were unsuccessful. Freezing point determination showed that this alkoxide does not crystallize, but instead becomes a glassy solid around −54° C.

Sodium 3,7-dimethyl-3-octanoxide was prepared in a method analogous to that described above for potassium 3,7-dimethyl-3-octanoxide by the addition of the alcohol to molten sodium in heptane in a high pressure reaction vessel. The sodium alkoxide was also isolated as a neat liquid product.

Lithium 3,7-dimethyl-3-octanoxide was prepared by the reaction of lithium hydride with 3,7-dimethyl-3-octanol in heptane, because of the relatively high melting point of lithium metal. Like the potassium and sodium compounds, the lithium alkoxide product was isolated as a neat liquid.

Other metal alkoxides isolated as a neat liquid include metal dimethylbenzenepropanoxides, metal 2-methyl-2-hexanoxides and metal 3,7-dimethyl-1,6-octene-3-oxides.

In the reactions of the present invention, addition of excess alcohol or incomplete reaction of the metal and alcohol can result in the formation of an insoluble solid alcoholate complex. Use of a slight excess of metal as well as longer reaction times can eliminate formation of the alcoholate complex.

EXPERIMENTAL EXAMPLES

Example 1

Potassium 3,7-Dimethyl-3-octanoxide, KDMO

Potassium metal (237 , 6.061 moles) was combined with heptane (1100 mL) in a high pressure reaction vessel and heated to approximately 110° C. with the back-pressure regulator set at 30 psig. The dry alcohol (886 g, 5.590 moles) was then slowly added into the reactor. During the reaction hydrogen gas was evolved. The alcohol was added over a 2 hours on the 1-gallon scale. Upon complete addition of the alcohol, the temperature was increased to approximately 125° C. for a period of 2 hrs to ensure the reaction went to completion. Evolved gas was noted after complete alcohol addition, but ceased shortly thereafter. The solution was then filtered resulting in a clear, water white potassium alkoxide solution.

Isolation of pure alkoxide potassium 3,7-dimethyl-3-octanoxide was accomplished by vacuum distillation of the heptane from the product. The liquid obtained was titrated for base content and found to be 99.3% pure. Spectral data are as follows: $^1$H NMR (250 MHz, $C_6D_6$) 1.82 (m), 1.43 (q, br), 1.37–1.24 (m), 1.14 (d), 1.00 (t) ppm; $^{13}$C NMR (62.9 MHz, $C_6D_6$) 71.7, 49.1, 42.9, 40.3, 34.5, 30.2, 25.5, 24.7, 11.5 ppm.

Example 2

Sodium 3,7-Dimethyl-3-octanoxide

Sodium hydride was combined with heptane in a round bottom flask and heated to approximately 100° C. The dry alcohol was then slowly added into the reaction mixture. During the addition hydrogen gas was evolved. Upon complete addition of the alcohol, the mixture was heated for a period of 1 hr to ensure the reaction proceeded to completion. This was confirmed by the lack of an alcohol hydroxyl peak in the infrared spectrum. The solution was then filtered, resulting in a pale yellow solution.

Isolation of pure alkoxide sodium 3,7-dimethyl-3-octanoxide was accomplished by vacuum distillation of the heptane from the product. The liquid obtained was titrated for base content and found to be 99.8% pure. Spectral data are as follows: $^1$H NMR (250 MHz, $C_6D_6$) 1.71–1.63 (m), 1.51–1.27 (m, br), 1.16 (s), 1.07–0.99 (multiple peaks) ppm; $^{13}$C NMR (62.9 MHz, $C_6D_6$) 69.6, 48.1, 40.9, 39.2, 28.5, 24.1, 23.0, 10.0 ppm.

Example 3

Lithium 3,7-Dimethyl-3-octanoxide

Lithium hydride and heptane were combined in a round bottom flask and heated to reflux. The dry alcohol was then slowly added into the mixture. Upon complete addition of the alcohol, the mixture was heated for a period of 1 hr to ensure the reaction proceeded to completion. The solution was then filtered resulting in a clear, pale yellow, lithium alkoxide solution.

Isolation of the pure alkoxide, lithium 3,7-dimethyl-3-octanoxide was accomplished by vacuum distillation of the heptane from the product. The liquid obtained was titrated for base content and found to be 98.7% pure. Spectral data are as follows: $^1$H NMR (250 MHz, $C_6D_6$) 1.71–1.54 (m), 1.46–1.31 (m), 1.08–0.98 (m); $^{13}$C NMR (62.9 MHz, $C_6D_6$) 71.4, 46.3, 40.5, 37.9, 30.8, 28.5, 24.3, 23.0, 10.5 ppm.

Example 4

Potassium 2-Methyl-2-hexanoxide

Potassium hydride was combined with THF in a round bottom flask. The alcohol, 2-methyl-2-hexanol, was then slowly added to the flask. During the addition hydrogen gas was evolved. The reaction mixture was stirred for 1 hour at ambient temperature to ensure the reaction proceeded to completion. The infrared spectrum confirmed the complete reaction of the alcohol. The solution was then filtered resulting in a clear, pale yellow solution.

Isolation of the pure alkoxide was accomplished by vacuum distillation of the THF from the product. Spectral data are as follows: 1H NMR (250 MHz, $C_6D_6$) 1.51 (p), 1.34–1.25 (m), 1.15 (t), 1.05 (s, br) ppm; $^{13}$C NMR (62.9 MHz, $C_6D_6$) 68.1, 50.1, 35.3, 28.8, 24.7, 14.9 ppm.

Example 5

Sodium 2-methyl-2-hexanoxide

Sodium hydride was combined with heptane in a round bottom flask. The alcohol, 2-methyl-2-hexanol, was then added to the slurry. No reaction occurred upon the addition of the alcohol to the hydride. The mixture was heated to reflux under nitrogen for a period of 2 hours to complete the reaction. The infrared spectrum confirmed complete reactivity of the alcohol. The solution was filtered, resulting in a clear, orange solution.

Isolation of the pure alkoxide was accomplished by vacuum distillation of the heptane from the product. Spectral data are as follows: $^1$H NMR (250 MHz, $C_6D_6$) 1.52 (m, br), 1.44 (m, br), 1.33 (s), 1.02 (t) ppm; $^{13}$C NMR (62.9 MHz, $C_6D_6$) 68.6, 50.7, 33.8, 29.7, 24.3, 14.5 ppm.

Example 6

Sodium Dimethylbenzenepropoxide

Sodium hydride (9.0 g, 0.375 moles) was combined with heptane (250 mL) in a high pressure reaction vessel and heated to 60° C. with the back-pressure regulator set to 26 psig. The alcohol, dimethylbenzenepropanol (32 g, 0.195 moles), was then slowly added (over a period of approximately 30 minutes) into the reactor. Upon complete addition of the alcohol, the temperature was increased to 100° C. for a period of 3 hours to ensure the reaction went to completion. The solution was then filtered resulting in a pale yellow solution.

Isolation of the pure alkoxide was accomplished by vacuum distillation of the heptane from the product. The liquid obtained was titrated for base content and found to be greater than 99% pure. Spectral data are as follows: $^1$H NMR (250 MHz, $C_6D_6$) 7.21–7.06 (m), 2.60–2.53 (m), 1.70 (m, br), 1.17 (s); $^{13}$C NMR (62.9 MHz, $C_6D_6$) 143.5, 128.7, peak under solvent, 125.9, 68.2, 53.6, 34.1 ppm.

Example 7

Lithium Dimethylbenzenepropoxide

Lithium hydride was combined with heptane in a high pressure reaction vessel and heated to 60° C. with the back-pressure regulator set to 26 psig. The alcohol, dimethylbenzenepropanol, was then slowly added into the reactor. Upon complete addition of the alcohol, the temperature was increased to 100° C. for a period of 2 hours to ensure the reaction went to completion. The solution was then filtered resulting in a pale yellow solution.

Isolation of the pure alkoxide was accomplished by vacuum distillation of the heptane from the product. The liquid obtained was titrated for base content and found to be 99.3% pure. Spectral data are as follows: $^1$H NMR (250 MHz, CDCl$_3$) 7.24–7.05 (m), 2.61–2.54 (m), 1.69–1.62 (m), 1.17 (s) ppm; $^{13}$C NMR (62.9 MHz, CDCl$_3$) 143.3, 128.6, 128.4, 125.8, 69.2, 50.9, 33.1 ppm.

Example 8

Potassium 3,7-Dimethyl-1,6-octene-3-oxide

Potassium metal was combined with heptane in a high pressure reaction vessel and heated to approximately 100° C. with the back-pressure regulator set at 25 psig. The dry alcohol (linalool) was then slowly added into the reactor. The alcohol was slowly added to the metal. Upon complete addition of the alcohol, the temperature was increased to approximately 120° C. for a period of 4 hrs to ensure the reaction went to completion. The solution was then filtered resulting in a clear, pale yellow potassium alkoxide solution.

Isolation of pure alkoxide was accomplished by vacuum distillation of the heptane from the product. The liquid obtained was titrated for base content and found to be 99.3% pure. Spectral data are as follows: $^1$H NMR (250 MHz, $C_6D_6$) 6.19 (m), 5.50 (m), 4.94 (m), 2.06 (m), 1.82 (t), 1.41 (m), 1.10 (s) ppm; $^{13}$C NMR (62.9 MHz, $C_6D_6$) 156.9, 129.8, peak under solvent, 106.3, 72.4, 49.2, 32.6, 26.1, 25.3, 17.9 ppm.

Example 9

Sodium 3,7-Dimethyl-1,6-octene-3-oxide

Sodium metal was combined with heptane in a high pressure reaction vessel and heated to approximately 105° C. with the back-pressure regulator set at 25 psig. The dry alcohol was then slowly added into the reactor. Upon complete addition of the alcohol, the temperature was increased to approximately 120° C. for a period of 4 hrs to ensure the reaction went to completion. The solution was then filtered resulting in a clear, pale yellow sodium alkoxide solution.

Isolation of pure alkoxide was accomplished by vacuum distillation of the heptane from the product. The liquid obtained was titrated for base content and found to be % pure. Spectral data are as follows: $^1$H NMR (250 MHz, $C_6D_6$) 6.17 (m, br), 5.46 (m, br), 5.15 (d), 4.98 (d), 2.14 (s, br), 1.78 (s), 1.70 (s), 1.39 (s, br) ppm; $^{13}$C NMR (62.9 MHz, $C_6D_6$) 153.2, 130.5, 125.9, 108.7, 71.1, 50.0, 29.1, 26.2, 25.9, 17.7 ppm.

Example 10

Lithium 3,7-Dimethyl-1,6-octene-3-oxide

Lithium hydride was combined with heptane in a high pressure reaction vessel with the back-pressure regulator set at 25 psig. The dry alcohol was then slowly added into the reactor while the reactor was heated. Upon complete addition of the alcohol, the reaction was heated at approximately 100° C. for a period of 4.5 hrs to ensure the reaction went to completion. The solution was then filtered resulting in a clear, pale yellow lithium alkoxide solution.

Isolation of pure alkoxide lithium 3,7-dimethyl-1,6-octene-3-oxide was accomplished by vacuum distillation of the heptane from the product. The liquid obtained was titrated for base content and found to be % pure. Spectral data are as follows: $^1$H NMR (250 MHz, $C_6D_6$) 6.11 (m, br), 5.27 (d), 5.04 (d), 2.10 (m), 1.71 (s), 1.63 (s), 1.35 (s, br) ppm; $^{13}$C NMR (62.9 MHz, $CDCl_3$) 150.4, 130.9, 125.3, 110.5, 71.5, 47.8, 28.7, 25.9, 24.9, and 17.9 ppm.

Although the present invention has been described in detail in connection with the above examples, it is to be understood that such detail is solely for that purpose and that variations can be made by those skilled in the art without departing from the spirit of the invention except as it may be limited by the following claims.

What is claimed is:

1. A compound having the formula $R^4_n$M-(3,7-dimethyl-3-octanoxide), wherein M is a group I metal, a group II metal or Zn, $R^4$ is an alkyl group or an alkoxyl group, n is 0 if the metal is monovalent, n is 1 if the metal is divalent, and wherein the compound is liquid at or below 25° C. and has a purity greater than 97 wt %.

2. The compound of claim 1 wherein the metal is K, Li, Na, Cs, Mg, Ca or Zn.

3. The compound of claim 1 wherein the metal is K, Na or Li.

4. The compound of claim 1 wherein the metal is K.

5. The compound of claim 1 wherein the metal is K, Li, Na, Cs, Ca or Zn.

* * * * *